United States Patent [19]

Cooper et al.

[11] Patent Number: 4,574,126

[45] Date of Patent: Mar. 4, 1986

[54] PYRIDINE DERIVATIVES HISTAMINE H$_2$-ANTAGONISTS

[75] Inventors: David G. Cooper, Letchworth; George S. Sach, Welwyn, both of England

[73] Assignee: Smith Kline & French Laboratories Limited, Welwyn Garden City, England

[21] Appl. No.: 473,520

[22] Filed: Mar. 9, 1983

[30] Foreign Application Priority Data

Mar. 17, 1982 [GB] United Kingdom ................ 8207835
Mar. 31, 1982 [GB] United Kingdom ................ 8209540

[51] Int. Cl.$^4$ .................. A61K 31/445; C07D 213/57; C07D 213/36
[52] U.S. Cl. .................................. 514/318; 514/343; 514/351; 514/357; 546/193; 546/281; 546/300; 546/330; 546/332
[58] Field of Search ............... 546/332, 330, 300, 281, 546/193; 424/263, 267; 514/318, 343, 351, 357

[56] References Cited

U.S. PATENT DOCUMENTS 4,250,316  2/1981  Algieri et al. ................ 546/287
4,252,819  2/1981  Hirata et al. ................ 424/285
4,490,533 12/1984  Bolhofer et al. ............. 546/332

OTHER PUBLICATIONS

Derwent Abstract 29067e (EP 49173), 4/7/82.
Derwent Abstract 20656d (Netherlands 8004967).
Derwent Abstract 55416e (EP 55179), 6/30/82.
Derwent Abstract 269k (EP 67436), 12/22/82.

Primary Examiner—Richard A. Schwartz
Attorney, Agent, or Firm—Joan S. Keps; Richard D. Foggio; Alan D. Lourie

[57] ABSTRACT

This invention relates to 2-pyridine derivatives substituted in the 4-position with a dialkylamino- or piperidinyl- or pyrrolidinylalkyl group. The compounds have histamine H$_2$-antagonist activity.

15 Claims, No Drawings

PYRIDINE DERIVATIVES HISTAMINE H₂-ANTAGONISTS

This invention relates to certain pyridine derivatives, processes for their preparation, pharmaceutical compositions containing them and their use as histamine H$_2$-antagonists.

A histamine, a physiologically active compound endogenous in mammals, exerts its action by interacting with certain sites called receptors. One type of receptor is known as a histamine H$_1$-receptor (Ash and Schild, Brit. J. Pharmac. Chemother. 27 427(1966)) and the actions of histamine mediated through these receptors are blocked by drugs commonly called "antihistamines" (histamine H$_1$-antagonists) a common example of which is mepyramine. A second type of histamine receptor is known as the H$_2$-receptor (Black et al. Nature 1972, 236, 385). These receptors are not blocked by mepyramine but are blocked by burimamide. Compounds which block these histamine H$_2$-receptors are called histamine H$_2$-antagonists.

Histamine H$_2$-antagonists are useful in treating disease conditions caused by the biological effects of histamine mediated through H$_2$-receptors, for example, as inhibitors of gastric acid secretion, in the treatment of inflammation mediated through histamine H$_2$-receptors and as agents which act on the cardiovascular system, for example, as inhibitors of effects of histamine on blood pressure mediated through histamine H$_2$-receptors.

Cimetidine is an example of a histamine H$_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine H$_1$- and H$_2$-receptors and blockade of both types of receptors is useful. These conditions include inflammation mediated by histamine, for example skin inflammation, and those hypersensitivity responses due to the action of histamine at H$_1$- and H$_2$-receptors, for example allergies.

According to the present invention there is provided compounds of formula (1):

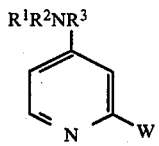

(1)

or a pharmaceutically acceptable salt thereof, where
R$^1$ and R$^2$ are the same or different and are C$_{1-6}$ alkyl or with the nitrogen atom to which they are attached form a pyrrolidino or piperidino group;
R$^3$ is C$_{1-4}$ alkylene;
W is a group —XYCH$_2$CH$_2$NHR$^4$ in which
Y is methylene or sulphur;
X is methylene or oxygen, provided that it is methylene when Y is sulphur, and
R$^4$ is a group of formula (2):

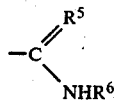

(2)

where R$^5$ is NCN, NNO$_2$, NH or CHNO$_2$ and R$^6$ is hydrogen, hydroxy, amino, C$_{1-6}$ alkyl, C$_{2-4}$ alkynyl; or R$^4$ is a group of formula (3):

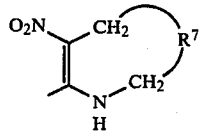

(3)

where R$^7$ is a covalent bond or methylene or ethane-1, 2-diyl optionally substituted with one C$_{1-6}$ alkyl group or a second C$_{1-6}$ alkyl group or a phenyl (C$_{1-6}$ alkyl) group, or a group of formula (4):

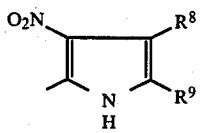

(4)

where R$^8$ is hydrogen; C$_{1-6}$ alkyl, optionally substituted phenyl or phenyl (C$_{1-6}$ alkyl), (the substituents being one or more C$_{1-6}$ alkyl or C$_{1-6}$ alkoxy groups or halogen atoms or a methylenedioxo group), or optionally substituted furanyl- or thienyl- or pyridyl(C$_{1-6}$ alkyl) (the substituents being one or more C$_{1-6}$ alkyl or C$_{1-6}$ alkoxy groups); and R$^9$ is hydrogen, C$_{1-6}$ alkyl or benzyl,
or W is Y$^1$R$^{10}$ where
Y$^1$ is (CH$_2$)$_a$ where a is from 3 to 6 or (CH$_2$)$_b$S(CH$_2$)$_d$ where b and d are the same or different and are from 1 to 3 or O(CH$_2$)$_f$ where f is from 2 to 5 and R$^{10}$ is a group of formula (5):

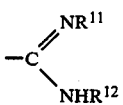

(5)

where R$^{11}$ is cyano, carbamoyl, ureido, hydroxy, C$_{1-6}$ alkoxy, C$_{1-6}$ alkanoyl, C$_{1-6}$ alkanoylamino, arylsulphamoyl, aralkanoyl, carboxymethyl or a group of formula (6):

(6)

where R$^{13}$ is C$_{1-6}$ alkyl, haloC$_{1-6}$alkyl, optionally subsituted phenyl, amino, mono or di(C$_{1-6}$)alkanoylamino, arylamino or arylalkanoylamino;
R$^{12}$ is hydrogen, C$_{1-6}$ alkyl, C$_{2-6}$ alkanoyl, C$_{2-6}$ alkenyl, C$_{2-6}$ alkynyl, cyano;
or R$^{10}$ is a group of formula —CONHR$^{14}$ where R$^{14}$ is hydrogen, C$_{1-6}$ alkyl, hydroxy or sulfamoyl.

The presence of the group R$^1$R$^2$NR$^3$ at position 4 of the 2-pyridyl moiety in the compounds of formula (1) confers a particularly favourable level of H$_2$-antagonist activity.

Examples of C$_{1-6}$ alkyl groups which R$^1$ and R$^2$ represent are methyl, ethyl, n-propyl and iso-propyl. Perferably $R^1$ and $R^2$ are the same $C_{1-6}$ alkyl group and in particular they are methyl.

Examples of alkylene groups which $R^3$ represents are methylene, ethane-1,2-diyl and propane-1,3-diyl. Preferably $R^3$ is methylene. Preferably the group $R^1R^2NR^3$ is dimethylaminomethyl.

One group of compounds falling within the scope of the invention has formula (1) where X is methylene and Y is sulphur.

A second group of compounds falling within the scope of the invention has formula (1) where X is oxygen and Y is methylene.

When $R^4$ is a group of formula (2), preferably $R^5$ is NCN or $CHNO_2$.

Examples of $C_{1-6}$ alkyl groups which $R^6$ represents are methyl, ethyl and n-propyl. Examples of $C_{2-6}$ alkynyl groups which $R^6$ represents are ethynyl and propynyl. Preferably $R^6$ is $C_{1-6}$ alkyl, particularly methyl.

When $R^4$ is a group of formula (3) it will be appreciated that where $R^7$ bears two substituents, these will be selected for stereochemical compatibility.

Examples of $C_{1-6}$ alkyl groups suitable as substituents on $R^7$ are methyl, ethyl and n-propyl.

Examples of specific values for $R^7$ are methylene, ethane-1,1-diyl and ethane-1,2-diyl.

Preferably $R^7$ is methylene.

Examples of substituted phenyl groups and the substituted phenyl moiety for phenyl($C_{1-6}$ alkyl) groups for $R^8$ are 3-methylphenyl, 3-methoxyphenyl, 3,4-dimethoxyphenyl and 3-chlorophenyl.

Examples of optionally substituted furanyl-, thienyl- and pyridyl($C_{1-6}$ alkyl) groups for $R^8$ are optionally substituted 2-furanyl-, 2-thienyl-, 2-pyridyl-, 3-pyridyl-, or 4-pyridyl($C_{1-6}$ alkyl) groups, and particularly 3-pyridyl-, 6-methyl-3-pyridyl- and 6-methoxy-3-pyridyl($C_{1-6}$ alkyl).

Examples of $C_{1-6}$ alkyl groups for $R^8$ and $R^9$ are methyl, ethyl and n-propyl.

Preferably $R^8$ is benzyl.

Preferably $R^9$ is hydrogen.

When W is a group of formula $Y^1R^{10}$ preferably $R^{11}$ is cyano, carbamoyl or a group $-SO_2R^{13}$ where $R^{13}$ is amino and preferably $R^{12}$ is hydrogen.

Preferably $Y^1$ is $(CH_2)S(CH_2)_2$.

Examples of particular compounds within the scope of this invention are:
N-cyano-N'-methyl-N''-[2-(4-dimethylaminomethyl-2-pyridylmethylthio)ethyl]guanidine,
1-nitro-2-methylamino-2-[2-(4-dimethylaminomethyl-2-pyridylmethylthio)ethylamino]ethylene,
and their pharmaceutically acceptable salts.

Examples of pharmaceutically acceptable acid-additional salts of compounds of formula (1) are those formed with hydrochloric, hydrobromic, sulphuric, phosphoric, acetic, citric, maleic, lactic, ascorbic and methanesulphonic acids.

Compounds of formula (1) where $R^4$ is a group of formula (2):

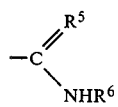
(2)

can be prepared by reacting a compound of formula (7):

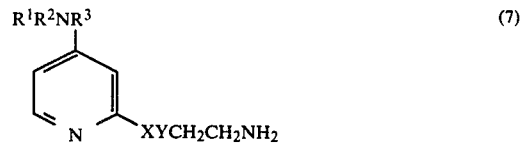
(7)

where $R^1$ to $R^3$ are as defined with reference to formula (1) with a compound of formula (8):

(8)

where $B^1$ is a group displaceable with amine, $B^2$ is a group displaceable by amine or is $NHR^6$ [where $R^6$ is as defined with reference to formula (2)] and $B^3$ is a group $R^5$ or $NCO_2C_6H_5$ and where $B^2$ is a group displaceable by amine, reacting with an amine of formula (9):

$R^6NH_2$ (9)

and where $B^3$ is $NCO_2C_6H_5$ and optionally when $B^3$ is NCN converting the group into NH.

Examples of leaving groups displaceable by amines are where $B^1$ or $B^2$ is QS—, QSO—, $QSO_2$—, or QO (Q being $C_{1-6}$ alkyl, aryl or aralkyl). Where $B^1$ or $B^2$ is QO—, Q is preferably phenyl. Preferably the group $B^1$ is QS— where Q is methyl. When $B^2$ is also a group displaceable by amine, preferably it is QSO where Q is methyl.

The displacement reaction is preferably carried out in the presence of a solvent, for example, a $C_{1-6}$ alkanol, at elevated temperatures for example the boiling point of the reaction mixture.

Compounds of formula (1) where $R^4$ is a group of formula (3) or (4) as previously defined can be prepared by reacting a compound of formula (10):

(10)

where $R^1$, $R^2$ and $R^3$ are as defined with reference to formula (1) and $A^1A^2$ is either a group $XYCH_2CH_2NH_2$ where X and Y are as defined with reference to formula (1) or, when X and Y in formula (1) represent methylene and sulphur respectively, $A^1$ is methylene and $A^2$ is a leaving group displaceable by thiol, with a compound of formula (11) or (12):

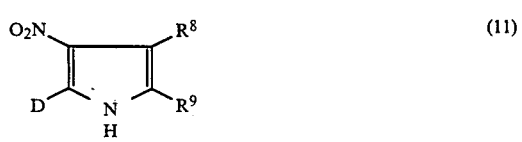
(11)

(12)

where D is either a group displaceable with amine when $A^1A^2$ $XYCH_2CH_2NH_2$, or is $HSCH_2CH_2NH-$ when $A^1$ is methylene and $A^2$ is a leaving group displaceable by thiol.

Examples of groups displaceable by thiol are hydroxy, alkanoyloxy (preferably acetoxy), methanesulphonyloxy, p-toluenesulphonyloxy, trifluoromethanesulphonyloxy, $C_{1-6}$ alkoxy (preferably methoxy), chlorine, bromine and triarylphosphonium (preferably triphenylphosphonium).

When $A^2$ is sulphonyloxy, chlorine, bromine or triarylphosphonium, the reaction is carried out in the presence of a base, for example in the presence of sodium ethoxide in ethanol. When $A^2$ is a group displaceable by mercaptan, preferably it is hydroxy, $C_{1-6}$ alkoxy or acetoxy and the reaction is carried out under acidic conditions, for example in acetic acid or in aqueous hydrochloric or hydrobromic acid.

Compounds of formula (7) where $R^3$ is $CH_2$ can be prepared as described in European patent application No. 0049173 and compounds of formula (7) where $R^3$ other than $CH_2$ can be prepared by analogous procedures. Thus the compounds of formula (7) can be made in one of three ways:

(i) for those compounds in which X is methylene and Y is sulphur; by reacting a pyridyl derivative of formula (10) (in which $A^1$ is methylene and $A^2$ is a group displaceable with a thiol) with cysteamine. Preferably $A^2$ is chlorine and the reaction is carried out under basic conditions, for example in a $C_{1-6}$ alkanol in the presence of an alkali metal alkoxide. When $A^2$ is hydroxy the reaction is preferably carried out under acidic conditions, for example in acetic, hydrobromic or hydrochloric acid.

Compounds of formula (10) in which $A^2$ is hydroxy can be prepared by hydroxymethylating a compound of formula (13),

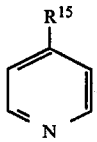  (13)

where $R^{15}$ is $R^{16}CN$ [(where $R^{16}$ is a covalent bond or $C_{1-3}$ alkylene) or $R^1R^2NR^3$ (where $R^1$ to $R^3$ are as defined for formula (1)], for example using methanol and ammonium persulphate. The product in which $R^{15}$ is $-R^{16}CN$ is then reduced, (for example using lithium aluminium hydride) and alkylated (for example when $R^1$ and $R^2$ are $C_{1-6}$ alkyl by reductive alkylation with hydrogen and an aldehyde). Optionally the products in which $A^2$ is hydroxy are converted into the corresponding compounds in which $A^2$ is chlorine or bromine by reaction with a thionyl halide, for example thionyl chloride in dichloromethane.

(ii) for those compounds in which X and Y are both methylene; by reducing a pyridyl derivative of formula (14), for example with lithium aluminium hydride.

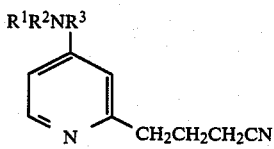  (14)

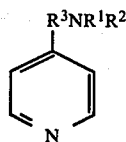  (15)

The compounds of formula (14) can be prepared by reacting a compound of formula (15) with 4-cyanobutyric acid, ammonium persulphate and silver nitrate.

(iii) for those compounds in which X is oxygen and Y is methylene; by reducing a compound of formula (16) (17), or (18):

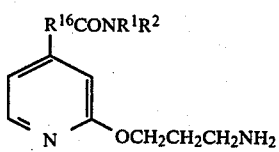  (16)

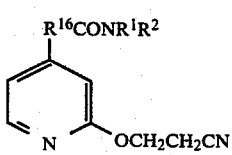  (17)

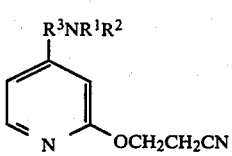  (18)

where $R^1$ to $R^3$ are as defined with reference to formula (1) and $R^{16}$ is a covalent bond or $C_{1-3}$ alkylene, using lithium aluminium hydride, or by reacting a compound of formula (19) with 3-aminopropanol under basic conditions.

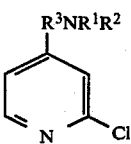  (19)

The compounds of formula (16), (17), and (18) can be prepared by reacting a compound of formula (20) or (21)

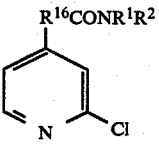  (20)

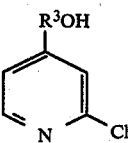  (21)

with 3-aminopropanol or 3-hydroxypropionitrile under basic conditions. The compounds of formula (19) can be prepared by successively reacting a compound of formula (21) with thionyl chloride and an amine $R^1R^2NH$.

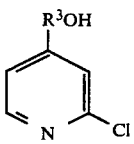

(21)

Compounds of formula (11) and (12) are known and can be prepared by known procedures as described in European patent application Nos. 5984, 5985, 28117 and 28482.

Compounds of formula (1) where W is $Y^1R^{10}$ and $R^{10}$ is a group of formula (5) can be prepared by reacting a compound of formula (22):

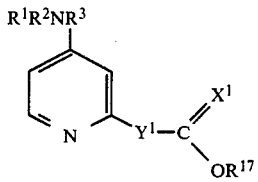

(22)

where $R^1$, $R^2$, $R^3$ and $Y^1$ are as defined with reference to formula (1); $R^{17}$ is $C_1$-$C_4$ alkyl, $X^1$ is oxygen, $NR^{11}$ or $NR^{12}$; where $R^{11}$ and $R^{12}$ are as defined with reference to formula (1) with an amine of formula $R^{11}NH_2$ or $R^{12}NH_2$ where $R^{11}$ and $R^{12}$ are as defined with reference to formula (1).

Compounds of formula (1) where W is a group of formula:

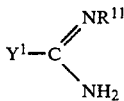

can be prepared by reacting a compound of formula (23):

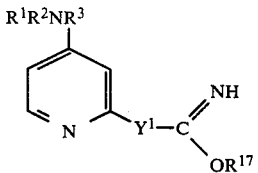

(23)

where $R^1$ to $R^3$ and $Y^1$ are as defined with reference to formula (1) and $R^{17}$ is $C_{1-6}$ alkyl, with an amine of formula $R^{11}NH_2$.

These reactions can be carried out in an organic solvent for example a $C_{1-6}$ alkanol (in particular methanol, ethanol, or propanol) chloroform, diethylether, tetrahydrofuran or benzene.

The reactions can be carried out at moderate temperature for example from ambient to the reflux temperature of the solvent.

The amines $R^{11}NH_2$ and $R^{12}NH_2$ are described in Belgian Patent No. 882071 and their reaction with compounds of formula (22) can be carried out in a same way as the analogous reacting described in this Belgian Patent.

Where one of the groups $R^{11}$ or $R^{12}$ in the compound of formula (1) so obtained is cyano, the cyano group can be converted into carbamoyl by reacting with dry hydrogen chloride in a $C_{1-6}$ alkanol and in particular methanol at reduced temperatures for example from 0°-5° C.

Where one of $R^{11}$ or $R^{12}$ in the compound of formula (1) is hydrogen it can be converted into $C_{1-6}$ alkanoyl by acylation with for example the $C_{1-6}$ alkanoylchloride.

Where $R^{11}$ in the compound of formula (1) so obtained is sulphamoyl and $R^{12}$ is hydrogen, the group =NH can be converted into keto (=O) by hydrolysis.

Intermediates of formula (23) can be prepared by analogy with known methods from the corresponding nitrile of formula (24):

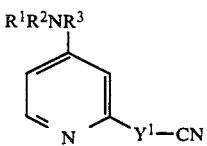

(24)

This in turn can be made as previously described herein for the preparation of compounds of formula (14) and (18) or by analogy with these methods.

Acid-addition salts of compounds of formula (1) can be formed from the corresponding bases by standard procedures for example by reacting the base with an acid in a $C_{1-6}$ alkanol or by the use of an ion-exchange resin. Salts of compounds of formula (1) can be interconverted using an ion-exchange resin.

The activity of the compounds of formula (1) as histamine $H_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

Inhibition of histamine-stimulated secretion of gastric acid can be measured by using a lumen-perfused stomachs of rats anaesthetised with urethane using the following modification of the method of Ghosh and Schild, Brit. J. Pharmac. Chemother. 13 54 (1958):

Female Sprague-Dawley rats (160–200 g) are starved overnight and anaesthetised with urethane given intraperitoneally in one dose (200 mg). The trachea and jugular veins are both cannulated and a mid-line incision is made in the abdomen exposing the stomach which is cleared from connective tissue. A small incision is made in the rumen of the stomach and the stomach is washed with 5% w/v glucose solution. The oesophagus is partially cleared of connective tissue and cannulated with polythene tubing and the oesophagus and vagi are then cut above the cannula. An incision is made in the antrum and a cannula is passed into the stomach via the ruminal incision and through into the antrum so that the head of the cannula lies in the body of the stomach. A funnel-shaped cannula is inserted in the ruminal incision and tied into position so that the line between the rumen and the body coincides with the edge of the funnel. The antral cannula is tied into place to reduce the possibility that antrally released gastrin will effect gastric acid secretion. Two stab wounds are made in the abdominal wall, and the stomach cannulae passed through. The stomach is perfused through the oesophageal and stomach cannulae with 5.4% w/v glucose solution at 37° at 1-2 ml min$^{-1}$. The effluent is passed over a micro-flow pH electrode and recorded by a pH meter fed to an anti-log unit and flat-bed recorder. The basal output of acid secretion from the stomach is monitored by measurement of the pH of the perfusion effluent. A sub-maximal dose of histamine is continuously infused into the jugular vein and produces a stable plateau of acid secretion and the pH of the perfusion effluent is determined when this condition is obtained. Infusion of histamine at a rate of 0.25 micromol kg$^{-1}$ min$^{-1}$ produces 70% of maximum histamine stimulated gastric acid secretion. The test compound is then administered intravenously into the second jugular vein and washed in with glucose solution (0.2 ml, 5.4% w/v). The difference in acid secretion between basal output and the histamine stimulated plateau level and the reduction of acid secretion caused by the test compound are calculated from the difference in pH of the perfusion effluent. ED$_{50}$ values (for inhibiting sub-maximal acid secretion by 50%) are determined by administering one dose of test compound to one rat and repeating this in at least four rats for each of three or more dose levels. The results obtained are then used to calculate the ED$_{50}$ value by the standard method of least squares.

Heidenhain pouch dogs can be prepared and used as described in European Specification No. 15138.

In the guinea pig atrium test a spontaneously beating isolated portion of the guinea pig right atrium is secured under tension (300 mg) between an anchorage and a transducer in a 15 ml tissue bath and immersed in McEwens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity (pA$_2$ value).

To illustrate the level of activity of the compounds of the invention we have determined that the products of Examples 1 and 2 have ED$_{50}$ values in the lumen-perfused rat test of less than 0.1 micromol kg$^{-1}$ i.v. and pA$_2$ values in the guinea pig atrium test of more than 7.0.

In order to use compounds of formula (1) or a pharmaceutically acceptable salt thereof for medical purposes, they are normally formulated in accordance with standard pharmaceutical practice as pharmaceutical compositions.

The invention further provides pharmaceutical compositions comprising a compound of formula (1) above or a pharmaceutically acceptable acid-addition salt thereof together with a pharmaceutically acceptable carrier.

Compounds of formula (1) and their pharmaceutically acceptable acid-addition salts may be administered orally, parenterally, cutaneously or rectally.

Compounds of formula (1) and their pharmaceutically acceptable salts which are active when given orally can be formulated as syrups, tablets, capsules and lozenges. A syrup formulation will generally consist of a suspension or solution of the compound or salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or salt in a sterile aqueous carrier or parenterally acceptable oil.

Typical compositions for administration to the skin include lotions and creams in which the compound of formula (1) or salt thereof is contained in a liquid vehicle.

A typical suppository formulation comprises a compound of formula (1) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains from 1.5 to 25 mg) of a compound of formula (1) or a pharmaceutically acceptable salt thereof calculated as the free base.

The invention also provides a method of blocking histamine H$_2$-receptors which comprises administering to an animal an effective amount to block said receptors of a compound of formula (1) or a pharmaceutically acceptable acid-addition salt thereof.

The daily dosage regimen for an adult patient is an oral dose of between 15 mg and 1500 mg and preferably between 20 mg and 250 mg or an intravenous, subcutaneous, or intramuscular dose of between 1.5 mg and 150 mg, and preferably between 5 mg and 20 mg of compound of formula (1) or pharmaceutically acceptable salt thereof calculated as the free base, the composition being administered 1 to 6 times per day.

The pharmaceutical compositions of the invention will normally be administered to man for the treatment of peptic ulcers and other conditions caused or exacerbated by gastric acidity in the same general manner as that employed for known histamine H$_2$-antagonists, due allowance being made in terms of dose levels for the potency of the compound of the present invention relative to known histamine H$_2$-antagonists.

The following Examples illustrate the invention.

EXAMPLES

EXAMPLE 1

(a) A solution of 2-(4-dimethylaminomethyl-2-pyridylmethylthio)ethylamine (1 g) in ethanol (10 ml)

was added over 10 minutes to a solution of dimethylcyanodithioimidocarbonate (0.71 g) in ethanol (15 ml). The solution was stirred for 30 minutes, evaporated to dryness and the residue purified by elution from a column of silica gel with 7.5% methanol/chloroform to yield N-cyano-S-methyl-N'-[2-(4-dimethylaminomethyl-2-pyridylmethylthio)ethyl]-isothiourea (0.97 g) as a clear oil.

(b) A solution of N-cyano-S-methyl-N'-[2-(4- dimethylaminomethyl-2-pyridylmethylthio)ethylamino]-isothiourea (0.92 g) in 16% methylamine in ethanol was allowed to stand at ambient temperature over 18 hours. The solvent was removed in vacuo and the residue purified by chromatography on silica gel eluted with 20% methanol/chloroform followed by recrystallisation from ethanol/ether 1:5 to yield N-cyano-N'-methyl-N''-[2-(4-dimethylaminomethyl-2- pyridylmethylthio)ethyl]-guanidine (0.48 g) as white prisms m.p. 114°–115.5°.

$C_{14}H_{22}N_6S$: found: C, 54.85%; H, 7.18%; N, 27.31%; S, 10.83%; requires: C, 54.87%; H, 7.24%; N, 27.43%; S, 10.46%;

EXAMPLE 2

(a) 2-(4-Dimethylaminomethyl-2-pyridylmethylthio)ethylamine (0.75 g) in methanol (10 ml) was added over 10 minutes to a solution of 1,1-dithiomethyl-2-nitroethylene monosulphoxide (0.655 g) in methanol (30 ml). The solution was stirred for 1.5 hours, evaporated to dryness and the residue was purified by chromtography on a silica gel column eluted with 10% methanol/chloroform to yield 1-[2-(4-dimethylaminomethyl-2-pyridylmethylthio)ethylamino]-1-methylthio-2-nitroethylene (0.85 g) as a clear oil.

(b) A solution of 1-[2-(4-dimethylaminomethyl-2-pyridylmethylthio)ethylamino]-1-methylthio-2-nitroethylene (0.85 g) in 16% methylamine in ethanol (40 ml) was allowed to stand at ambient temperature for 36 hours. The solvent was removed in vacuo and the product was purified by chromatography on a silica gel column eluted with 15% methanol/chloroform followed by recrystallisation from acetonitrile to give 1-nitro-2-methylamino-2-[2-(4-dimethylaminomethyl-2-pyridylmethylthio)ethylamino]-ethylene (0.32 g) m.p. 113°–115° C.

EXAMPLE 3

A solution of 2-(4-dimethylaminomethyl-2-pyridylmethylthio)ethylamine (0.325 g) and 2-methylsulphinyl-3-nitropyrrole (0.25 g) was refluxed in ethanol (12 ml) over 6 days. The solution was evaporated to dryness and the residue was chromatographed on silica gel eluted with 10% methanol/chloroform to give 2-[2-(4-dimethylaminomethyl-2-pyridylmethylthio)ethylamino]-3-nitropyrrole (0.072 g) as a yellow solid m.p. 90°–95° C. dec.

EXAMPLE 4

(a) 4-Dimethylaminomethyl-2-chloromethylpyridine dihydrochloride is reacted with thiourea in ethanol under reflux. Removal of the ethanol yields 4-dimethylaminomethyl-2-pyridylmethyl isothiourea trihydrochloride.

(b) 4-Dimethylaminomethyl-2-pyridylmethyl isothiourea trihydrochloride in ethanol is reacted with 3-chloropropionitrile under nitrogen and in the presence of sodium hydroxide in water to give 3-(4-dimethylaminomethyl-2-pyridylmethylthio)propionitrile.

(c) 3-(4-Dimethylaminomethyl-2-pyridylmethylthio)propionitrile in a mixture of dry methanol and dry chloroform under nitrogen at 2° C. is treated with dried hydrogen chloride gas and allowed to stand at ca. 0° C. to give after basification with ice cold potassium carbonate solution methyl 3-(4-dimethylaminomethyl-2-pyridylmethylthio)propionimidate. The solvents are removed at reduced pressure and the residue reacted with cyanamide in dry methanol. The solvent is removed under reduced pressure and the residue is treated with cold aqueous potassium carbonate. Extraction of the organic component of the mixture so produced with chloroform and concentration of the chloroform extract gives a residue which is reacted with methanolic methylamine to give N-cyano-N'-methyl-3-(4-dimethylaminomethyl-2-pyridylmethylthio)propionamidine.

EXAMPLE 5

A solution of N-cyano-N'-methyl-3-(4-dimethylaminomethyl-2-pyridylmethylthio)propionamidine in methanol/choloform is cooled to 0°–5° C. and through it is passed hydrogen chloride gas. Removal of the solvent at reduced pressure yields after being left to stand N-carbamoyl-N'-methyl-3-(4-dimethylaminomethyl-2-pyridylmethylthio) propionamidine.

EXAMPLE 6

3-(4-Dimethylaminomethyl-2-pyridylmethylthio)propionitrile in a mixture of dry methanol and dry chloroform under nitrogen at 2° C. is treated with dried hydrogen chloride gas and allowed to stand at ca. 0° C. to give after basification with ice cold potassium carbonate solution methyl-3-(4-dimethylaminomethyl-2-pyridylmethylthio)propionimidate which is reacted in methanol with sulphamide under reflux. Evaporation of the solvent at reduced pressure and purification of the product by chromatography yields N-sulphamoyl-3-(4-dimethylaminomethyl-2-pyridylmethylthio)propionamidine.

EXAMPLE 7

(a) 3-(4-Dimethylaminomethyl-2-pyridylmethylthio)propionitrile in a mixture of dry methanol and dry chloroform under nitrogen at 2° C. is treated with dried hydrogen chloride gas and allowed to stand at ca. 0° C. to give after treatment with cold potassium carbonate solution and solvent extraction methyl-3-(4-dimethylaminomethyl-2-pyridylmethylthio)propionimidate.

(b) Methyl-3-(4-dimethylaminomethyl-2-pyridylmethylthio)propionimidate is added to a methanol solution of cyanamide. After standing overnight N-cyano-3-(4-dimethylaminomethyl-2-pyridylmethylthio)propionamidine is obtained.

EXAMPLE 8

A solution of N-cyano-3-(4-dimethylaminomethyl-2-pyridylmethylthio)propionamidate in methanol/chloroform is cooled to 0°–5° C. and through it is passed hydrogen chloride gas. Removal of the solvent at reduced pressure yields N-carbamoyl-5-(4-dimethylaminomethyl-2-pyridylmethylthio)propionamidine.

EXAMPLE 9

(a) Ammonium persulphate in water and 5-cyanopentanoic acid in water are added separately and simultaneously over 30 minutes to a mixture of 4-dimethylaminomethylpyridine silver nitrate, water and concentrated sulphuric acid stirred at 80°. The reaction mixture is stirred at 80° for 1.5 hours, cooled, poured onto crushed ice and aqueous ammonia. The solution is extracted with chloroform and the chloroform extracts are washed with dilute sodium hydroxide, dried over magnesium sulphate, and concentrated in vacuo to give 5-(4-dimethylaminomethyl-2-pyridyl)pentanonitrile.

(b) 5-(4-Dimethylaminomethyl-2-pyridyl)pentanonitrile in a mixute of dry methanol and dry chloroform under nitrogen at 2° C. is treated with dried hydrogen chloride gas and allowed to stand at ca. 0° C. to give after treatment with cold potassium carbonate solution and solvent extraction methyl-5-(4-dimethylaminomethyl-2-pyridyl)pentanoimidate.

(c) Methyl-5-(4-dimethylaminomethyl-2-pyridyl)pentanoimidate is added to a methanol solution of cyanamide. After standing overnight N-cyano-5-(4-dimethylaminomethyl-2-pyridyl)pentanoamidine is obtained.

EXAMPLE 10

A solution of N-cyano-5-(4-dimethylaminomethyl-2-pyridyl)pentanoamidine in methanol/choloform is cooled to 0°–5° C. and through it is passed hydrogen chloride gas. Removal of the solvent at reduced pressure yields after leaving the residue to stand N-carbamoyl-5-(4-dimethylaminomethyl-2-pyridyl)pentanoamidine.

EXAMPLE 11

(a) A solution of 2-(4-piperidinomethyl-2-pyridylmethylthio)ethylamine (2.65 g) in ethanol (25 ml) was added over 30 minutes to a solution of dimethylcyanodithioimidocarbonate (3 g) in ethanol (40 ml). The solution was stirred for 1 hour, evaporated to dryness and the residue chromatographed on silica, eluted with chloroform-methanol to give N-cyano-S-methyl-N'-[2-(4-piperidinomethylthio)ethyl]isothiourea (3.12 g) as a clear oil.

(b) A solution of N-cyano-S-methyl-N'-[2-(4-piperidinomethylthio)ethyl]isothiourea (1.01 g) in 33% methylamine in ethanol (25 ml) was allowed to stand at room temperature for 16 hours. The solvent was removed in vacuo and the residue purified by chromatography on silica gel eluted with chloroform-methanol followed by recrystallisation from chloroform-pentane to give N-cyano-N'-methyl-N''-[2-(4-piperidinomethyl-2-pyridylmethylthio)ethyl]-guanidine (0.73 g) as a colourless solid m.p. 79°–81° C.

$C_{17}H_{26}N_6S$: Found: C, 58.96%; H, 7.54%; N, 24.32%; S, 9.23%. requires: C, 58.93%; H, 7.56%; N, 24.26%; S, 9.25%.

EXAMPLE 12

3-[4-(1-Piperidinomethyl)pyridyl-2-oxy]propylamine (1.18 g), 2-methylsulphinyl-3-nitropyrrole (0.75 g) and ethanol (40 ml) were refluxed for three days. The reaction mixture was evaporated to dryness and the dark brown residue purified by chromatography on silica gel using chloroform-methanol as eluent. After recrystallisation from ethyl acetate-ether 2-(3-[4-(1-piperidinomethyl)-pyridyl-2-oxy]propylamino)-3-nitropyrrole was obtained as a yellow solid m.p. 106.5°–108.5° C., (0.16 g).

$C_{18}H_{25}N_5O_3$: Found: C, 60.05%; H, 7.05%; N, 19.10%. requires: C, 60.15%; H, 7.01%; N, 19.49%.

EXAMPLE 13

2-(4-Dimethylaminomethylpyrid-2-ylmethylthio)ethylamine (1.0 g) was dissolved in ethanol (40 ml), and 2-methylsulphinyl-3-nitro-4-benzylpyrrole (0.92 g) was added. The solution was stirred under reflux for 48 hours and the ethanol was distilled off to leave an oily residue which was purified by chromatography using chloroform-ethanol as eluent. After crystallisation from isopropanol 2-[2-(4-dimethylaminomethylpyrid-2-ylmethylthio)ethyl]amino-3-nitro-4-benzylpyrrole (0.108 g) m.p. 126°–127° C. was obtained.

EXAMPLE 14

Pharmaceutical Compositions

A pharmaceutical composition for oral administration is prepared containing

| | | % by weight |
|---|---|---|
| A | N—cyano-N'—methyl-N''—[2-(4-dimethylaminomethyl-2-pyridylmethylthio)ethyl] guanidine | 55 |
| | Dibasic calcium phosphate dihydrate | 20 |
| | Approved coloring agent | 0.5 |
| | Polyvinylpyrrolidone | 4.0 |
| | Microcrystalline Cellulose | 8.0 |
| B | Maize Starch | 8.0 |
| | Sodium glycollate | 4.0 |
| | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dired granules and compressing the mixture into tablets containing 100 mg, 150 mg or 200 mg of the free base.

A pharmaceutical composition for injectable administration is prepared by converting N-cyano-N'-methyl-N''-[2-(4-dimethylaminomethyl-2-pyridylmethylthio)ethyl] guanidine into the hydrochloride salt form and dissolving this in sterile pyrogen-free water to give a 1 to 5% w/w solution. The solution is clarified by filtration and filled into vials which are sealed and sterilised. A suitable vial contains 2 ml of the solution.

We claim:

1. A compound of the formula (1):

or a pharmaceutically acceptable salt thereof, where
$R^1$ and $R^2$ are the same or different and are $C_{1-6}$ alkyl or with the nitrogen atom to which they are attached form a pyrrolidino or piperidino group;
$R^3$ is $C_{1-4}$ alkylene;
W is a group —$XYCH_2CH_2NHR^4$ in which
Y is methylene or sulphur;
X is methylene or oxygen, provided that it is methylene when Y is sulphur, and
$R^4$ is a group of formula (2):

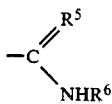 (2)

where $R^5$ is NCN, $NNO_2$, NH or $CHNO_2$ and $R_6$ is hydrogen, hydroxy, amino, $C_{1-6}$ alkyl or when Y is methylene, $C_{2-4}$ alkynyl except that $R^5$ is not NH when $R^6$ is hydrogen.

2. A compound according to claim 1, where $R^1$ and $R^2$ are the same and are $C_{1-6}$ alkyl.

3. A compound according to claim 2, where $R^1$ and $R^2$ are both methyl.

4. A compound according to claim 1, where $R^3$ is methylene.

5. A compound according to claim 4, where $R^1R^2NR^3$ is dimethylaminomethyl.

6. A compound according to claim 1, where X is methylene and Y is sulphur.

7. A compound according to claim 1, where X is oxygen and Y is methylene.

8. A compound according to claim 1, where $R^5$ is —NCN.

9. A compound according to claim 8, where $R^5$ is —$CHNO_2$.

10. A compound according to claim 8, where $R^6$ is $C_{1-6}$ alkyl.

11. A compound according to claim 10, where $R^6$ is methyl.

12. A compound according to claim 1 selected from the group consisting of N-cyano-N'-methyl-N''-[2-(4-dimethylaminomethyl-2-pyridylmethylthio)ethyl] guanidine or a pharmaceutically acceptable salt thereof.

13. A compound according to claim 1 selected from the group consisting of 1-nitro-2-methylamino-2-[2-(4-dimethylaminomethyl-2-pyridylmethylthio)ethylamino] ethylene or a pharmaceutically acceptable salt thereof.

14. A pharmaceutical composition having histamine $H_2$-antagonist activity comprising an amount of a compound according to claim 1 sufficient to block histamine $H_2$-receptors and a pharmaceutically acceptable carrier.

15. A method for blocking histamine $H_2$-receptors which comprises administering to an animal an effective amount to block said receptors of a compound of claim 1.

* * * * *